(12) United States Patent
Hughes

(10) Patent No.: US 7,060,288 B2
(45) Date of Patent: Jun. 13, 2006

(54) BIOMEDICAL DEVICES

(76) Inventor: Timothy Charles Hughes, 22 Crusoe Drive, Lysterfield, Victoria 3156 (AU)

( * ) Notice: Subject to any disclaimer, the term of this patent is extended or adjusted under 35 U.S.C. 154(b) by 505 days.

(21) Appl. No.: 10/080,245

(22) Filed: Feb. 21, 2002

(65) Prior Publication Data

US 2002/0151972 A1      Oct. 17, 2002

(30) Foreign Application Priority Data

Feb. 28, 2001      (EP)      .................................. 01810205

(51) Int. Cl.
*A61F 2/00*      (2006.01)
*A61F 2/14*      (2006.01)
(52) U.S. Cl. ...................... 424/427; 424/422; 424/424; 424/429; 623/4.1; 623/5.11; 623/6.11; 623/6.23
(58) Field of Classification Search ................ 424/429, 424/428, 484, 422–424, 427; 427/39.9; 623/4.1, 623/5.11, 6.11, 6.23
See application file for complete search history.

(56) References Cited

U.S. PATENT DOCUMENTS 5,945,498 A * 8/1999 Hopken et al. ................ 528/42
6,099,852 A * 8/2000 Jen ............................. 424/429
6,121,341 A     9/2000 Sawhney et al. ............. 522/84

FOREIGN PATENT DOCUMENTS

| WO | WO 00/29548 A | 5/2000 |
| WO | WO 00/71180 A | 11/2000 |
| WO | WO 00/72052 A | 11/2000 |

OTHER PUBLICATIONS

International Search Report.

* cited by examiner

*Primary Examiner*—Michael Hartley
*Assistant Examiner*—Micah-Paul Young
(74) *Attorney, Agent, or Firm*—Foley & Lardner LLP

(57) ABSTRACT

The present invention is concerned with biomedical device comprising (a) a biocompatible organic or inorganic bulk material and
(b) a coating comprising polymerizable carbon-carbon double bonds covalently attached to at least part of the bulk surface.

The biomedical devices of the invention are radiation sensitive and may be used, for example, as ready-to-use corneal onlay in ophthalmic surgery.

19 Claims, No Drawings

BIOMEDICAL DEVICES

The present invention relates to a ready-to-use biomedical device that may be fixed to tissue by means of an adhesive, which can be cured on demand. Particularly, it relates to a ready-to-use corneal onlay, which may be fixed to the corneal basement membrane upon irradiation with a light source.

It is desirable in many applications, especially in the biomaterial and medical field to adhere biomaterials and other materials or devices to tissue. Tissue is defined as any part of the body, living or dead. A biomedical device that can be glued directly to tissue and attains sufficient interfacial bond strength is attractive because it may obviate the need for surgical methods such as suturing. Useful applications include the adhesion of drug delivery devices to the epidermis, the gluing of anti-adhesion barriers for surgery and the adhesion of synthetic onlays to cornea. Conventional surgical adhesives are often not suitable for a wide range of adhesive applications. Currently cyanoacrylates and fibrin glues are used clinically as soft tissue adhesives. However the brittleness of cured adhesives, the potential toxicity of their biodegradation products and the lack of control over cure time are the major drawbacks of cyanoacrylates.

A variety of different methods for the bonding of devices to tissue have been disclosed in the prior art. For example, U.S. Pat. No. 5,354,336 describes a method for sealing lenticules onto a corneal surface comprising the steps of placing the lenticule to correct position, applying a polymerizable collagen composition onto the lenticule and the corneal surface to form a collagen coating over the lenticule and the corneal surface and polymerizing the coating in the presence of an initiator thereby sealing the lenticule onto the corneal surface. However said glues have not yet proven satisfactory mainly because of severe handling problems. For example, the surgeon always has to mix the glue components prior to use. Once the premixing has taken place, only a limited time period is available for using the glue depending on the glue's specific curing time; this puts time-pressure on the surgeon. Following the attachment of the onlay onto the cornea, excessive glue has to be removed carefully otherwise glue residues may inhibit the normal function of biological tissue. Further disadvantages of the known glues concern, for example, insufficient mechanical stability and adhesive duration. In view of these and other drawbacks, there is clearly a need for a "cure on demand" biomedical device.

Surprisingly, it now has been found that biomedical devices, in particular corneal onlays comprising a suitable biocompatible bulk material, may be attached conveniently to living tissue if they comprise certain polymerizable carbon-carbon double bonds covalently attached to the surface of said bulk material.

The present invention therefore in one aspect relates to a biomedical device comprising
  (a) a biocompatible organic bulk material and
  (b) a coating comprising polymerizable carbon-carbon double bonds covalently attached to at least part of the bulk surface.

Preferred embodiments of the invention concern biomedical devices obtainable by processes as outlined below.

A preferred process comprises the steps of
  (a1) providing a biomedical device comprising functional groups on its surface, and
  (b1) covalently attaching a multifunctional compound comprising at least one polymerizable carbon-carbon double bond and at least one additional functional group that is coreactive to the functional groups of the surface of the biomedical device.

A particularly preferred process comprises the steps of
  (a1) providing a biomedical device comprising functional groups on its surface, and
  (b2) covalently coupling functional groups of the surface of the medical device with a natural or synthetic polymer comprising co-reactive groups, and
  (b3) covalently coupling a multifunctional compound comprising at least one polymerizable carbon-carbon double bond and at least one additional functional group that is coreactive to the reactive groups of said natural or synthetic polymer.

Examples of bulk materials that may be coated according to the process of the invention are natural or synthetic organic polymers, or laminates, composites or blends of said materials. Some examples of polymers are polyaddition and polycondensation polymers (polyurethanes, epoxy resins, polyethers, polyesters, polyamides, polycarbonates and polyimides); vinyl polymers (polyacrylates, polymethacrylates, polystyrene, polyethylene, polyacrylamides and halogenated derivatives thereof, polyvinyl acetate and polyacrylonitrile); elastomers (silicones, polybutadiene and polyisoprene); or modified or unmodified biopolymers (collagen, cellulose, chitosan and the like).

Another preferred group of bulk materials are those conventionally used for the manufacture of biomedical devices, e.g. contact lenses, intraocular lenses or artificial cornea, which are not hydrophilic per se. Such materials are known to the skilled artisan and may comprise for example polysiloxanes, perfluoropolyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene propylene, or tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another preferred group of biocompatible polymers are those being conventionally used for the manufacture of biomedical devices, e.g. contact lenses, which are hydrophilic per se, since hydrophilic groups, e.g. carboxy, carbamoyl, sulfate, sulfonate, phosphate, amine, ammonium or hydroxy groups, are inherently present in the material. Such materials are known to the skilled artisan and comprise for example polyhydroxyethyl acrylate, poly-hydroxyethyl methacrylate (HEMA), polyvinyl pyrrolidone (PVP), polyacrylic acid, polymeth-acrylic acid, polyacrylamide, poly-N,N-dimethyl acrylamide (DMA), polyvinyl alcohol, copolymers for example from two or more monomers from the group hydroxyethyl acrylate, hydroxyethyl methacrylate, N-vinyl pyrrolidone, acrylic acid, methacrylic acid, acrylamide, N,N-dimethyl acrylamide, vinyl alcohol, vinyl acetate and the like, polyalkylene glycols such as polyethylene glycols, polypropylene glycols or polyethylene/polypropylene glycol block copolymers. Typical examples are e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon or Atlafilcon.

An even more preferred group of bulk materials are, for example, porous polymers with improved wettability and cell growth ability as described in WO 97/35906 or in WO 00/15686.

The surface of the bulk material may inherently contain functional groups or may be provided with covalently attached functional groups, for example, by plasma deposition. The method of coating a surface by plasma deposition is well known to the skilled artisan and is described in, e.g. WO 98/52620 and WO 00/29548. Typical examples of reactive groups being introduced to the surface of the bulk material by plasma surface preparation include aldehyde groups, amino groups, hydroxy groups, carboxy groups, carbonyl groups, sulfonic acid groups, sulfonyl chloride groups and groups able to be replaced by amino or hydroxy groups, such as halo groups. Aldehyde groups, thiol groups, amino groups, hydroxy groups and carboxy groups are preferred.

Examples of natural or synthetic polymer used in step (b2) are cell-adhesive glycoproteins like collagens (various types), fibronectin, vitronectin, laminin, poly(ethyl imine), amino dextran, PAMAM dendrimers, poly(allyl amine), poly(vinyl alcohol), poly(arylic acid) and poly(methacrylic acid). Collagen and collagen-like proteins are preferred. The coupling of cell-adhesive glycoproteins to plasma polymers covalently bound to the underlying bulk material is known and described, for example, in WO 00/29548.

Multifunctional compounds comprising at least one polymerizable carbon-carbon double bond to be coupled with functional groups covalently attached to the surface of a biomedical device, or to be covalently coupled to a natural or synthetic polymer are, for example, compounds of formula

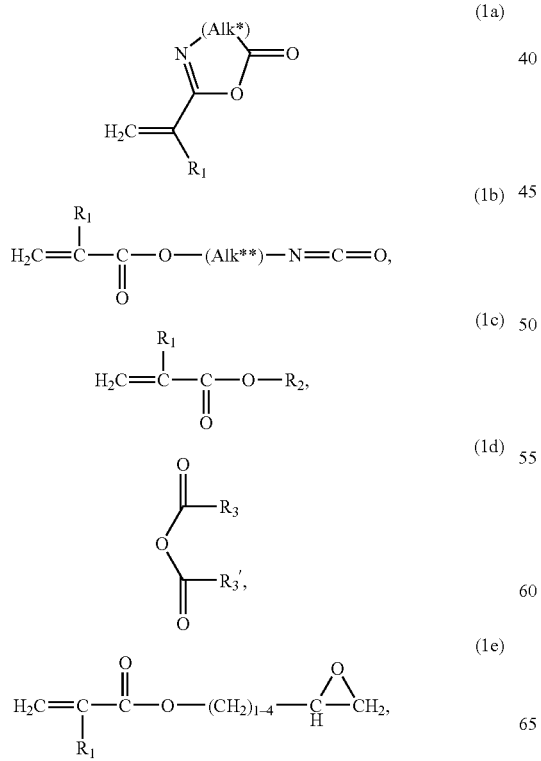

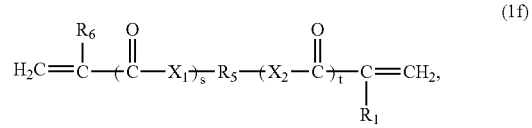

wherein $R_1$ is hydrogen, $C_1$–$C_4$-alkyl or halogen;

$R_2$ is hydrogen, unsubstituted or hydroxy-substituted $C_1$–$C_6$-alkyl or phenyl;

$R_3$ and $R_3'$ are each an ethylenically unsaturated radical having from 2 to 6 C-atoms, or $R_3$ and $R_3'$ together form a bivalent radical —C($R_4$)=C($R_4'$)— wherein $R_4$ and $R_4'$ are each independently of the other hydrogen, $C_1$–$C_4$-alkyl or halogen; and (Alk*) is $C_1$–$C_6$-alkylene, and (Alk**) is $C_2$–$C_{12}$-alkylene;

$R_5$ is a bivalent organic radical, which may be substituted, for example, by one or more acrylate, methacrylate, acrylamide, methacrylamide, vinyl or styryl functional groups.

$R_6$ is hydrogen, methyl or phenyl;

s and t independently of each other is an integer 0 or 1;

$X_1$ and $X_2$ are each independently from the other, O, NH, or N—$C_1$–$C_4$-alkyl; and $R_7$ is a carboxy derivative.

The following preferences apply to the variables contained in formulae (1a)–(1g):

$R_1$ is preferably hydrogen or $C_1$–$C_4$-alkyl, in particular hydrogen or methyl.

$R_2$ is preferably hydrogen or hydroxy-$C_1$–$C_4$-alkyl, in particular hydrogen or β-hydroxyethyl.

$R_3$ and $R_3'$ are preferably each vinyl or 1-methylvinyl, or $R_3$ and $R_3'$ together form a radical —C($R_4$)=C($R_4'$)—; wherein $R_4$ and $R_4'$ are each independently hydrogen or methyl.

(Alk*) is preferably methylene, ethylene or 1,1-dimethyl-methylene, in particular a radical —CH$_2$— or —C(CH$_3$)$_2$—.

(Alk**) is preferably $C_2$–$C_4$-alkylene and in particular 1,2-ethylene.

X is preferably NH or in particular O.

Examples of bivalent organic radicals $R_5$ are, for example, an optionally branched $C_1$–$C_{12}$-alkylene; a radical of dendrimer or star bust polymer; a radical of a polyethylene glycol; a radical of a polyvinyl alcohol, for example, a polyvinyl alcohol with pendant polymerisable groups as described in WO 96/24075; or a radical of a hyperbranched polyester resin as described by M. Johansson and A. Hult in Journal of Coatings Technology, 67, No. 849, 35 (1995).

$R_6$ is preferably hydrogen or methyl.

Examples of suitable carboxy derivatives $R_7$ are an acid halide, for example, —COCl or —COBr; or an ester or amide, preferably an activated derivative thereof.

$R_7$ as an activated ester or amide is, for example, a radical of formula

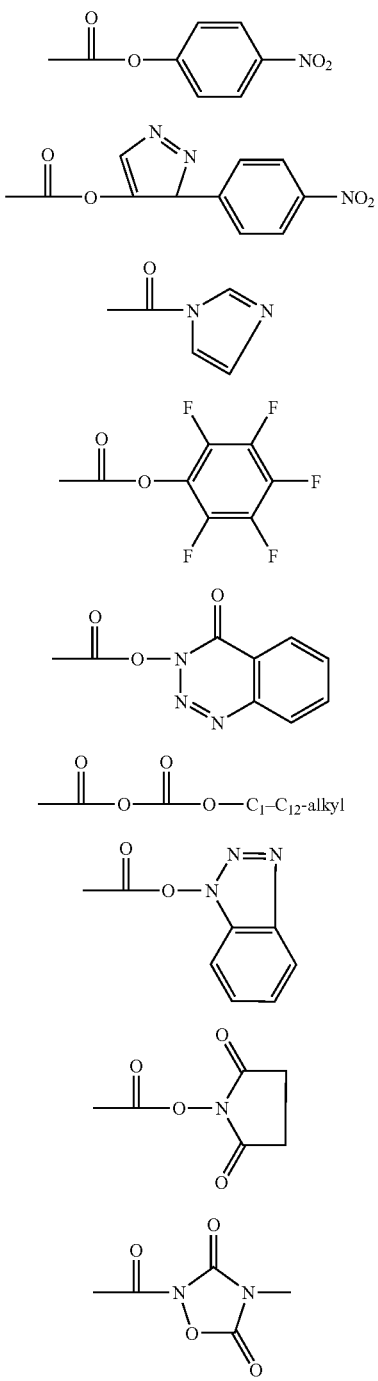

A preferred activated carboxy derivative is of formula (2a), (2d) or, in particular, of formula (2h).

Preferred vinyl monomers having a reactive group are 5,5-dimethyl-2-vinyl-oxazolin-4-one, 2-isocyanatoethylmethacrylate (IEM), acrylic acid, methacrylic acid, acrylic anhydride, maleic acid anhydride, 2-hydroxyethylacrylate (HEA), 2-hydroxyethylmethacrylate (HEMA), glycidylacrylate or glycidylmethacrylate, polyethylene glycol(dimethacrylate), polyethylene glycol(diacrylate), particularly preferred are 5,5-dimethyl-2-vinyl-oxazolin-4-one and 2-isocyanatoethylmethacrylate (IEM).

The method of attaching a bifunctional compound of formula (1a)–(1f) to a bulk material surface provided with coreactive functional groups or to a natural or synthetic polymer comprising coreactive functional groups depends on the nature of the reactive groups being present in compounds (1a)–(1e) and at the surface of said bulk material or natural or synthetic polymer.

In case that a compound of formula (1a) has to be coupled to the surface of a bulk material or to a natural or synthetic polymer containing amino groups, the reaction may be carried out advantageously at room temperature or at elevated temperature, for example at about 20 to 75° C., in water, in a suitable organic solvent or mixtures thereof, for example in an aqueous medium or in an aprotic polar solvent such as DMF, DMSO, dioxane, acetonitrile and the like.

In case that a compound of formula (1a) has to be coupled to the surface of a bulk material or to a natural or synthetic polymer containing hydroxy groups, aprotic polar solvents are preferred.

In case that a compound of formula (1b) has to be coupled to the surface of a bulk material or to a natural or synthetic polymer containing amino or hydroxy groups, the reaction may be carried out in an inert organic solvent such as acetonitrile, an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone or even a lower alcohol or water, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. In addition, the reaction of the isocyanato groups with amino groups may also be carried out in an aqueous solution in the absence of a catalyst. It is advantageous to carry out the above reactions under an inert atmosphere, for example under a nitrogen or argon atmosphere.

In case that a carboxy compound of formula (1c) has to be coupled to the surface of a bulk material or to a natural or synthetic polymer containing amino, thiol or hydroxy groups, or a hydroxy compound of formula (1c) with carboxy groups of the surface, the reaction may be carried out under the conditions that are customary for ester or amide formation. It is preferred to carry out the esterification or amidation reaction in the presence of an activating agent, for example N-ethyl-N'-(3-dimethyl aminopropyl)carbodiimide (EDC), N-hydroxy succinimide (NHS) or N,N'-dicyclohexyl carbodiimide (DCC).

In case that a compound of formula (1d) has to be coupled to the surface of a bulk material or to a natural or synthetic polymer containing amino, thiol or hydroxy groups the reaction may be carried out as described in organic textbooks, for example in an aprotic solvent, for example one of the above-mentioned aprotic solvents, at a temperature from room temperature to about 100° C.

In case that a compound of formula (1e) has to be coupled to the surface of a bulk material or to a natural or synthetic polymer containing amino, thiol or hydroxy groups, the reaction may be carried out, for example, at room temperature or at elevated temperature, for example at about 20 to 100° C., in an aprotic medium using a base catalyst, for example $Al(O-C_1-C_6\text{-alkyl})_3$ or $Ti(O-C_1-C_6\text{-alkyl})_4$.

In case that a compound of formula (1f) has to be coupled to the surface of a bulk material or to a natural or synthetic polymer containing amino, thio or hydroxy groups, the Michael-type addition reaction may be carried out, for example, at room temperature, for example at about 20 to 100° C., in an aprotic or protic medium.

In case that a compound of formula (1g) has to be coupled to the surface of a bulk material or to a natural or synthetic polymer containing amino, thiol or hydroxy groups, the reaction may be carried out, for example, at room temperature or at elevated temperature, for example at about 20 to 100° C., in an aprotic medium.

The fixation of a biomedical device such as a corneal onlay according to the present invention on the cornea may be initiated, for example, by irradiation, particularly by irradiation with UV or visible light. Preferably, the cornea is previously prepared for the attachment of the onlay, for example by removing the epithelial cell layers of the cornea by scraping.

The tissue to which the device is to be attached and also the device itself may optionally be treated with an initiator or catalyst to promote the adhesion of the device to the tissue surface. The initiator may be used at any concentration that does not have a detrimental effect on the device or the tissue. The term "initiator" is used herein in a broad sense, in that it is a composition, which under appropriate conditions will result in the polymerisation of a monomer. The use of a photo-initiator is preferred. Any of the photo-initiators found in the art may be suitable, if they are biocompatible and adhere to the particular surface. Examples are photo-oxidisable and photo-reducible dyes that may be used to initiate polymerisation, for example, acridine dyes; for example, acriblarine; thiazine dyes, for example, thionine; xanthine dyes, for example, rose Bengal; and phenazine dyes, for example, methylene blue. Other initiators include camphorquinones and acetophenone derivatives. A preferred photo-initiator for biological use is Eosin Y, which absorbs strongly to most tissue and is an efficient photo-initiator.

Any of the compounds typically used in the art as radical generators or co-initiators in photo-initiation may be used. These include co-catalysts or co-initiators such as amines, for example triethanolamine, as well as other trialkyl amines and trialkylol amines; sulfur compounds; heterocycles, for example, imidazole; enolates; organometallics; and other compounds, such as N-phenyl glycine.

In general, the onlay is placed in intimate contact with the corneal tissue and is then irradiated. Suitable light sources for the irradiation are known to the artisan and comprise for example mercury lamps, high pressure mercury lamps, xenon lamps, carbon arc lamps or sunlight. Sensitizers may be used to shift the irradiation wavelength. In addition, a suitable filter may be used to limit the irradiation to a specific wavelength range. Preferably, the onlay surface to which have been previously applied the compound(s) comprising radicals of formula (1) is irradiated with light of a wavelength $\geqq 300$ nm, preferably from 350 to 400 nm. The time period of irradiation is not critical but is usually in the range of up to 30 minutes, preferably from 10 seconds to 10 minutes, and more preferably from 15 seconds to 5 minutes, and particularly preferably from 30 seconds to 1.5 minutes.

The biomedical devices of the invention provide a new route towards implanting a corneal onlay onto a cornea which is easy to perform, does not affect the wearers vision, and is safe. In particular, a mechanically stable fixation of the implant on the cornea is obtained which lasts for a period of time sufficient for normal biological function to recover after surgery.

This may include the chance to allow the epithelial cells to recover, grow over the implant and thus fix it in a persistent manner. The onlays are very easy to handle, since the use thereof does not involve, for example, a premixing of glue components or time pressure upon the surgeon due to specific curing times of the glue components. In addition, no tedious removal of excess glue after fixing the onlay onto the cornea is necessary, and the previous problem of inhibition of overgrowth by glue residues does not exist. Moreover, the onlays of the invention may be stored conveniently for a long time, for example in form of a patch with cover foils protecting the surface(s). The onlay is then immediately ready for use, by just removing the cover foil(s) from the surface(s). All of the advantages mentioned above naturally apply not only to contact lenses but also to other biomedical moldings according to the invention as mentioned before.

The present invention is further described by the following non-limiting examples. If not specified otherwise, all parts are by weight. Temperatures are in degree Celsius.

EXAMPLE A-1

Lenticule Functionalization Using
2-vinyl-5,5-dimethyl-oxazolin-4-one on Collagen Six lenticules that have a thin coating of collagen on both sides are equilibrated into methanol from PBS (phosphate buffered saline). The methanol is exchanged for acetonitrile via a graded exchange of 25%, 50%, 75% and 100% acetonitrile. The lenticules are then individually treated with a 10% (v/v) solution of 2-vinyl-5,5-dimethyl-oxazolin-4-one in acetonitrile (8 ml) at room temperature with gentle shaking for 4 hours. The 2-vinyl-5,5-initiation4-one solutions are removed and replaced with acetonitrile. The lenticules are shaken overnight with fresh acetonitrile. The next morning lenticules are again shaken with fresh acetonitrile for 8 hours. The lenticules are taken through a graded exchange with 25%, 50%, 75% and 100% deionized water.

EXAMPLE A-2

Lenticule Functionalization Using polyethylene
glycol(diacrylate) [PEG(diacrylate)] ($M_W$ 700) on
Collagen Six lenticules that have a thin coating of collagen on both sides are equilibrated into water/methanol (50:50) from PBS (phosphate buffered saline) The lenticules are then individually treated with a 10% (v/v) solution of PEG(diacrylate) ($M_W$ 700) in water/methanol (50:50) (8 ml) at room temperature with gentle shaking for 24 hours. PEG(diacrylate) solutions are removed and replaced with methanol. The lenticules are shaken overnight with fresh methanol. The lenticules are taken through a graded exchange with 25%, 50%, 75% and 100% deionized water.

EXAMPLE B-1

In Situ Curing of Azlactone Modified Lenticules

Freshly slaughtered bovine eyes are debrided of their epithelium. A 1 mg/ml solution of Eosin Y (Aldrich) in deionized water is prepared and kept away from light. The debrided bovine cornea are treated with the Eosin Y solution (about 1–3 ml) for 1 minute. Freshly prepared modified lenticules from Example A-1 are treated with the Eosin Y solution for 1 minute. The excess solution is removed by absorption onto lint-free tissue paper. The lenticules are placed on the eye and any excess fluid or bubbles under the lenticule gently removed by wiping firmly across the top surface of the lenticule with a smooth object. The eye is irradiated with light from a xenon discharge lamp (greater than 1 Watt) for 1 min at a distance of 1 cm. After irradiation the lenticule can not be removed by a jet of water. The edges are firmly bound to the cornea and resisted lifting when the cornea is prodded. When attempts are made to remove the lenticule with tweezers it tears indicating the adhesives strength to the cornea is greater than the cohesive strength of the onlay.

EXAMPLE B-2

In Situ Curing of PEG(diacrylate) Modified Lenticules

Freshly slaughtered bovine eyes are debrided of their epithelium. A 1 mg/ml solution of Eosin Y (Aldrich) in deionized water is prepared and kept away from light. The debrided bovine cornea are treated with the Eosin Y solution (about 1–3 ml) for 1 minute. Freshly prepared modified lenticules from Example A-2 are treated with the Eosin Y solution for 1 minute. The excess solution is removed by absorption onto lint-free tissue paper. The lenticules are placed on the eye and any excess fluid or bubbles under the lenticule gently removed by wiping firmly across the top surface of the lenticule with a smooth object. The eye is irradiated with light from a xenon discharge lamp (greater than 1 Watt) for 1 min at a distance of 1 cm. After irradiation the lenticule cannot be removed by a jet of water. The edges are firmly bound to the cornea and resisted lifting when the cornea is prodded. When attempts are made to remove the lenticule with tweezers it tears indicating the adhesives strength to the cornea is greater than the cohesive strength of the onlay.

EXAMPLE B-3

Cytotoxicity Testing of Modified Lenticules

Both PEG(diacrylate) and azlactone modified lenticules from Examples B-1 and B-2 are tested for cytotoxicity. They both pass direct contact assays and cell growth inhibitor assay.

EXAMPLE B-4

Organ Culture Testing of Modified Lenticules

Organ Culture General Procedure

A corneal organ culture system originally developed by Foreman et al. [D. M. Foreman, S. Pancholi, J. Jarvis-Evans, D. McLeod, M. E. Boulton, A simple organ culture model for assessing the effects of growth factors on corneal re-epithelialization, Exp. Eye Res. 62, 555–564 (1996)], is modified to evaluate polymers and adhesive formulations aimed at ophthalmic applications that require epithelialization. The corneal organ culture utilizes bovine eyes enucleated from freshly slaughtered animals which are surgically wounded and then implanted with polymer lenticules with and without adhesive formulations. Following wounding and implantation, the corneas are excised from the eyeballs with a 5 mm scleral rim intact and transferred directly onto individual pre-formed agar plugs which provide support and maintain corneal curvature during the culture period. Agar plugs are pre-prepared using a 1:1 mixture of double strength serum-free medium with additives (see below) and 2% agar (Bacto-Agar from Difco, Australia) in distilled water. This is allowed to gel in moulds created by inverting previously-excised bovine corneas. Wounded corneas on their agar plugs are placed in individual petri dishes with 5 ml complete serum-free culture medium, which is sufficient to bring the medium to the level of the scleral rim. Culture medium used throughout is Dulbecco's Modification of Eagles Medium containing 20 mM L-glutamine (ICN Biomedicals, USA) with 120 ug/ml Penicillin G 200 ug/ml Streptomycin sulphate, 5 ug/ml Amphotericin B and ITS Premix (Collaborative Biomedical Products, Becton Dickinson USA) to a final concentration of 5 µg/ml of insulin and transferrin and 5 ng/ml of selenous acid. Samples are incubated for 8 days at 37° C. in 5% $CO_2$ in air with once daily medium changes washed over the corneal surface to remove desquamating epithelial cells from the anterior ocular surface. The growth of epithelium over the lenticule surface is monitored daily using a stereomicroscope. Corneas are fixed in 10% neutral buffered formalin after 8 days and paraffin histology is used to examine the structure and morphology of the migrating epithelium and the condition of the underlying stromal tissue.

This system has been shown to model the in vivo wound healing process and has utility in the evaluation of candidate polymers, surface treatments and adhesives for certain ophthalmic applications.

Organ Culture Testing of Azlactone Modified Lenticules

Azlactone modified lenticules (prepared as in Example B-1) were implanted using a superficial keratomoy and onlay (debridement) surgical models in organ culture using the above procedure. The wound bed was treated with Eosin Y solution (1 mg/ml) in deionized water for 2 minutes before placement of lenticule into the wound bed. The eye was irradiated with light from a Prolite light source (Dentsply Model 301 with an intensity of 78 mW/cm$^2$) for 2 min at a distance of 1 cm.

Clinically azlactone modified lenticules cured to the wound bed in the onlay model are fully covered with epithelium by day 6.5. Histology on one of these samples show complete coverage of the lenticule by corneal epithelium consisting of 1–2 layers of epithelial cells with some evidence of differentiation in the basal cell layer. There is no evidence of cytotoxicity to the adhesive. In most places the lenticule is firm on the stromal surface, indicating adhesion between the posterior face of the lenticule and the stromal wound bed.

Clinically azlactone modified lenticules implanted in a superficial keratomoy wound bed are fully covered with epithelium by day 6. A Histological sample shows complete coverage of the lenticule by corneal epithelium consisting of 3–4 layers of epithelial cells with some evidence of differentiation in the basal cell layer. There is no evidence of cytotoxicity to the adhesive. As with the onlay model, the lenticule is firm on the stromal surface indicating adhesion between the posterior face of the lenticule and the stromal wound bed.

Organ Culture Testing of PEG(diacrylate) Modified Lenticules

PEG (diacrylate) modified lenticules (prepared as in Example B-2) are implanted using a superficial keratomoy and onlay (debridement) surgical models in organ culture using above procedure. The wound bed was treated with eosin Y solution (1 mg/ml) in deionized water for 2 minutes before placement of lenticule into the wound bed. The eye is irradiated with light from a Prolite light source (Dentsply Model 301 with an intensity of 78 mW/cm²) for 2 min at a distance of 1 cm.

Clinically PEG (diacrylate) modified lenticules cured to the wound bed in the onlay model are fully covered with epithelium by day 4–5. Histology shows the epithelium in these cases is composed of 5–7 layers of epithelial cells with columnar basal cells (i.e. normal looking epithelium). There are no epithelial cells underneath the lenticule in either case suggesting that the PEG (diacrylate) provided adhesion between the lenticule and the anterior stroma.

Clinically PEG(diacrylate) modified lenticules implanted in a superficial keratomoy wound bed are fully covered with epithelium by day 7. Histology of this sample shows 5 layers of epithelial cells on the wound bed. Histology shows that this epithelium was confined to the anterior surface, with none underneath, and is composed of 4–5 layers of epithelial cells with some evidence of differentiation in the basal cell layer.

PEG(diacrylate) modified lenticules supported epithelialisation in both onlay and superficial keratomoy surgical models when tested in organ culture without any apparent cytotoxicity.

EXAMPLE B-5

In vivo Curing of Modified Lenticules

Felines are anaesthetized using an intramuscular injection of 10–15 mg/kg bodyweight ketamine and 1 mg/kg bodyweight xylazine to a depth of stage 3-plane 2. The corneal surface is lightly marked in the centre using an 8 mm diameter trephine and the corneal epithelium within this area is debrided using a beaver blade to expose the basement membrane. A 1 mg/ml solution of Eosin Y (Aldrich) in deionized water is prepared and kept away from light. The debrided feline cornea are treated with the Eosin Y solution (about 1–3 ml) for 1 minute. Freshly prepared modified lenticules from Example A-1 are treated with the Eosin Y solution for 1 minute. The excess solution is removed by absorption onto lint-free tissue paper. The lenticules are placed on the eye and any excess fluid or bubbles under the lenticule gently removed by wiping firmly across the top surface of the lenticule with a smooth object. The eye is irradiated with light from a Prolite light source (Densply Model 301 with an intensity of 78 mW/cm²) for 2 min at a distance of 1 cm. After irradiation the lenticule cannot be removed by a jet of water. The edges are firmly bound to the cornea and resisted lifting when the cornea is prodded. The lenticule is held in place for greater than 6 days and the eyes are quiet.

The invention claimed is:

1. A biomedical device comprising
   (a) a biocompatible organic bulk material, wherein the biocompatible organic bulk material is selected from the group consisting of a polysiloxane, perfluoroalkyl polyether, fluorinated poly(meth)acrylate, polyalkyl (meth)acrylate, a fluorinated polyolefin; and
   (b) a coating covalently attached to at least part of the bulk surface, wherein said coating comprises polymerizable carbon-carbon double bonds, and wherein the coating is obtained by covalently coupling functional groups of the surface of the medical device with a multifunctional compound comprising at least one polymerizable carbon-carbon double bond and at least one additional functional group that is coreactive to the functional groups of the device surface.

2. The biomedical device according to claim 1, which is an ophthalmic device.

3. The ophthalmic device according to claim 2, which is a contact lens, intraocular lens, corneal onlay, corneal implant, or an artificial cornea.

4. A biomedical device comprising
   (a) a biocompatible organic bulk material, wherein the biocompatible organic bulk material is selected from the group consisting of a polysiloxane, perfluoroalkyl polyether, fluorinated poly(meth)acrylate, polyalkyl (meth)acrylate, a fluorinated polyolefin; and
   (b) a coating covalently attached to at least part of the bulk surface, wherein said coating comprises polymerizable carbon-carbon double bonds, wherein the coating is obtained by covalently coupling functional groups of the surface of the medical device with a natural or synthetic polymer comprising co-reactive groups, and covalently coupling a multifunctional compound comprising at least one polymerizable carbon-carbon double bond and at least one additional functional group to said natural or synthetic polymer.

5. The biomedical device according to claim 1, wherein the multifunctional compound is selected from the group consisting of a compound of formula

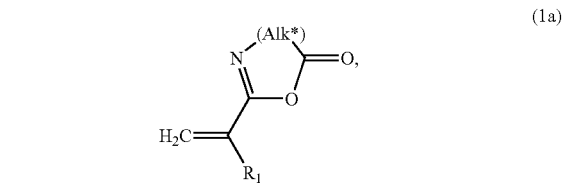

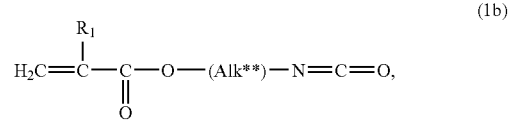

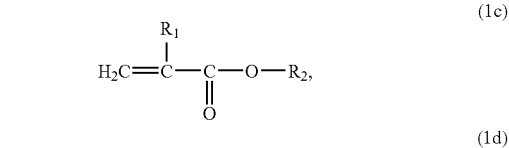

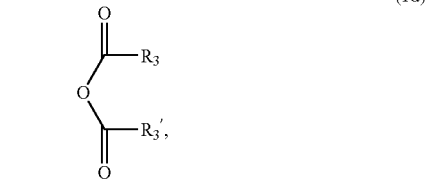

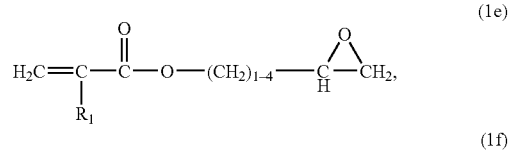

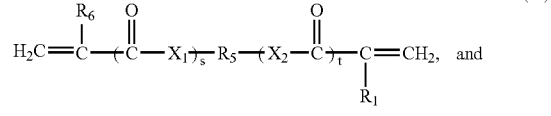

wherein $R_1$ is hydrogen, $C_1$–$C_4$-alkyl or halogen;

$R_2$ is hydrogen, unsubstituted or hydroxy-substituted $C_1$–$C_6$-alkyl or phenyl;

$R_3$ and $R_3'$ are each an ethylenically unsaturated radical having from 2 to 6 C-atoms, or $R_3$ and $R_3'$ together form a bivalent radical —C($R_4$)=C($R_4'$)— wherein $R_4$ and $R_4'$ are each independently hydrogen, $C_1$–$C_4$-alkyl or halogen and (Alk*) is $C_1$–$C_6$-alkylene, and (Alk**) is $C_2$–$C_{12}$-alkylene;

$R_5$ is a bivalent organic radical, which may be substituted;

$R_6$ is hydrogen, methyl or phenyl;

s and t independently of each other is an integer 0 or 1;

$X_1$ and $X_2$ are each independently from the other, O, NH, or N—$C_1$–$C_4$-alkyl; and $R_7$ is a carboxy derivative.

6. The biomedical device according to claim 4, wherein the multifunctional compound is selected from the group consisting of a compound of formula

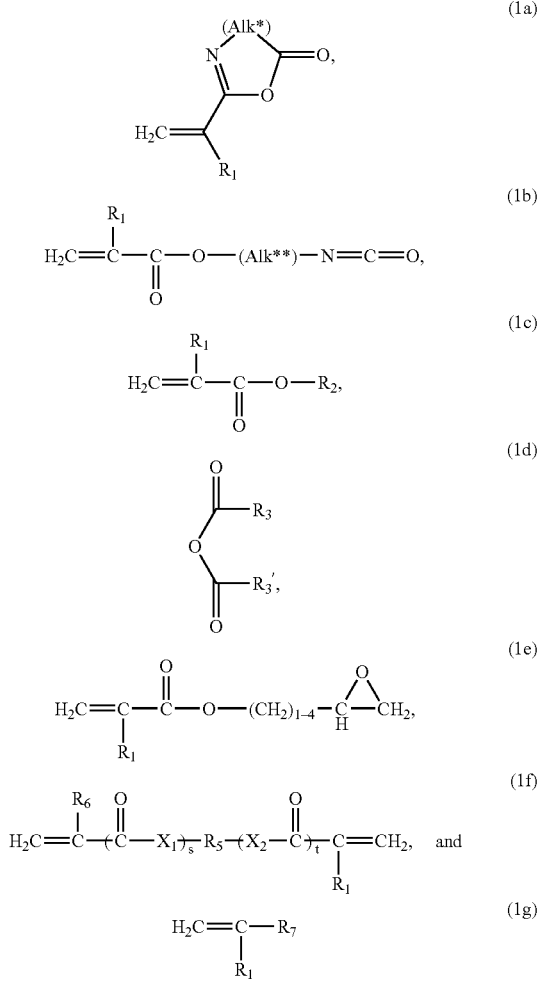

$R_1$ is hydrogen, $C_1$–$C_4$-alkyl or halogen;

$R_2$ is hydrogen, unsubstituted or hydroxy-substituted $C_1$–$C_6$-alkyl or phenyl;

$R_3$ and $R_3'$ are each an ethylenically unsaturated radical having from 2 to 6 C-atoms, or $R_3$ and $R_3'$ together form a bivalent radical —C($R_4$)=C($R_4'$)— wherein $R_4$ and $R_4'$ are each independently hydrogen, $C_1$–$C_4$-alkyl or halogen and (Alk*) is $C_1$–$C_6$-alkylene, and (Alk**) is $C_2$–$C_{12}$-alkylene;

$R_5$ is a bivalent organic radical, which may be substituted;

$R_6$ is hydrogen, methyl or phenyl;

s and t independently of each other is an integer 0 or 1;

$X_1$ and $X_2$ are each independently from the other, O, NH, or N—$C_1$–$C_4$-alkyl; and $R_7$ is a carboxy derivative.

7. The biomedical device according to claim 6, wherein the natural or synthetic polymer is a glycoprotein.

8. The biomedical device according to claim 7, wherein the glycoprotein is a collagen.

9. The biomedical device according to claim 8, wherein the multifunctional compound is a compound of formula (1a) or (1b).

10. The biomedical device according to claim 9, which is an ophthalmic device.

11. The opththalmic device according to claim 10, which is a contact lens, an intraocular lens or an artificial cornea.

12. A process for obtaining a biomedical device according to claim 1 by coating a biomedical device the process comprising the steps of (a) providing a biomedical device comprising functional groups on its surface, and (b) covalently attaching a multifunctional compound comprising at least one polymerizable carbon-carbon double bond and at least one additional functional group that is coreactive to the functional groups of the surface of the biomedical device.

13. A process for obtaining a biomedical device according to claim 6 by coating a biomedical device the process comprising the steps of (a) providing a biomedical device comprising functional groups on its surface, and (b) covalently coupling functional groups of the surface of the medical device with a natural or synthetic polymer comprising co-reactive groups, and (c) covalently coupling a multifunctional compound comprising at least one polymerizable carbon-carbon double bond and at least one additional functional group that is coreactive to the reactive groups of said natural or synthetic polymer.

14. The process for the coating of a biomedical device according to claim 12, wherein the multifunctional compound is selected from the group consisting of a compound of formula

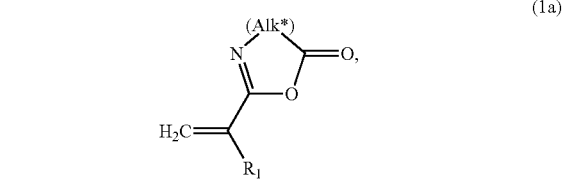

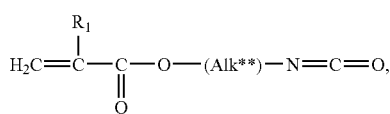

-continued $$\text{(1c)} \quad H_2C=\underset{R_1}{C}-\underset{\|}{C}-O-R_2,$$

$$\text{(1d)} \quad \text{(anhydride with } R_3 \text{ and } R_3')$$

$$\text{(1e)} \quad H_2C=\underset{R_1}{C}-\underset{\|}{C}-O-(CH_2)_{1-4}-\underset{H}{C}-CH_2,$$

$$\text{(1f)} \quad H_2C=\underset{R_1}{C}-(\underset{\|}{C}-X_1)_s-R_5-(X_2-\underset{\|}{C})_t-C=CH_2, \text{ and}$$

$$\text{(1g)} \quad H_2C=\underset{R_1}{C}-R_7$$

wherein $R_1$ is hydrogen, $C_1$–$C_4$-alkyl or halogen;

$R_2$ is hydrogen, unsubstituted or hydroxy-substituted $C_1$–$C_6$-alkyl or phenyl;

$R_3$ and $R_3'$ are each an ethylenically unsaturated radical having from 2 to 6 C-atoms, or $R_3$ and $R_3'$ together form a bivalent radical —$C(R_4)$=$C(R_4')$— wherein $R_4$ and $R_4'$ are each independently hydrogen, $C_1$–$C_4$-alkyl or halogen and (Alk*) is $C_1$–$C_6$-alkylene, and (Alk**) is $C_2$–$C_{12}$-alkylene;

$R_5$ is a bivalent organic radical, which may be substituted;

$R_6$ is hydrogen, methyl or phenyl;

s and t independently of each other is an integer 0 or 1;

$X_1$ and $X_2$ are each independently from the other, O, NH, or N—$C_1$–$C_4$-alkyl; and $R_7$ is a carboxy derivative.

15. The process for the coating of a biomedical device according to claim 13, wherein the multifunctional compound is selected from the group consisting of a compound of formula $$\text{(1a)}$$

$$\text{(1b)} \quad H_2C=\underset{R_1}{C}-\underset{\|}{C}-O-(Alk**)-N=C=O,$$

-continued $$\text{(1c)} \quad H_2C=\underset{R_1}{C}-\underset{\|}{C}-O-R_2,$$

$$\text{(1d)}$$

$$\text{(1e)} \quad H_2C=\underset{R_1}{C}-\underset{\|}{C}-O-(CH_2)_{1-4}-\underset{H}{C}-CH_2,$$

$$\text{(1f)} \quad H_2C=\underset{R_1}{C}-(\underset{\|}{C}-X_1)_s-R_5-(X_2-\underset{\|}{C})_t-C=CH_2, \text{ and}$$

$$\text{(1g)} \quad H_2C=\underset{R_1}{C}-R_7$$

wherein $R_1$ is hydrogen, $C_1$–$C_4$-alkyl or halogen;

$R_2$ is hydrogen, unsubstituted or hydroxy-substituted $C_1$–$C_6$-alkyl or phenyl;

$R_3$ and $R_3'$ are each an ethylenically unsaturated radical having from 2 to 6 C-atoms, or $R_3$ and $R_3'$ together form a bivalent radical —$C(R_4)$=$C(R_4')$— wherein $R_4$ and $R_4'$ are each independently hydrogen, $C_1$–$C_4$-alkyl or halogen and (Alk*) is $C_1$–$C_6$-alkylene, and (Alk**) is $C_2$–$C_{12}$-alkylene;

$R_5$ is a bivalent organic radical, which may be substituted;

$R_6$ is hydrogen, methyl or phenyl;

s and t independently of each other is an integer 0 or 1;

$X_1$ and $X_2$ are each independently from the other, O, NH, or N—$C_1$–$C_4$-alkyl; and $R_7$ is a carboxy derivative.

16. The process for the coating of a biomedical device according to claim 14, wherein the multifunctional compound is of formula (1a) or (1b).

17. The process for the coating of a biomedical device according to claim 15, wherein the multifunctional compound is of formula (1a) or (1b).

18. The method of using a medical device according to claim 1 as an intraocular lens, which comprises implanting the device into or onto the cornea.

19. The biomedical device according to claim 4, which is an ophthalmic device.

* * * * *